US009181565B2

(12) United States Patent
Tobey

(10) Patent No.: US 9,181,565 B2
(45) Date of Patent: Nov. 10, 2015

(54) SULFUR MANAGEMENT FOR PROCESSES AND CONTROL SYSTEMS FOR THE EFFICIENT ANAEROBIC CONVERSION OF HYDROGEN AND CARBON OXIDES TO ALCOHOLS

(71) Applicant: Richard E. Tobey, St. Charles, IL (US)

(72) Inventor: Richard E. Tobey, St. Charles, IL (US)

(73) Assignee: COSKATA, INC., Warrenville, IL (US)

( * ) Notice: Subject to any disclaimer, the term of this patent is extended or adjusted under 35 U.S.C. 154(b) by 138 days.

(21) Appl. No.: 13/836,923

(22) Filed: Mar. 15, 2013

(65) Prior Publication Data

US 2014/0272926 A1    Sep. 18, 2014

(51) Int. Cl.
| | | |
|---|---|---|
| *C12Q 3/00* | (2006.01) | |
| *C12Q 1/02* | (2006.01) | |
| *C12P 7/08* | (2006.01) | |
| *C12M 1/00* | (2006.01) | |
| *C12M 1/34* | (2006.01) | |
| *C12P 7/02* | (2006.01) | |
| *C12P 7/06* | (2006.01) | |

(52) U.S. Cl.
CPC *C12P 7/08* (2013.01); *C12M 21/00* (2013.01); *C12M 41/00* (2013.01); *C12M 43/00* (2013.01); *C12P 7/02* (2013.01); *C12P 7/065* (2013.01); *C12Q 1/02* (2013.01); *C12Q 3/00* (2013.01)

(58) Field of Classification Search
None
See application file for complete search history.

(56) References Cited

U.S. PATENT DOCUMENTS

| | | |
|---|---|---|
| 2010/0047886 A1 | 2/2010 | Hickey et al. |
| 2010/0298450 A1 | 11/2010 | Datta et al. |
| 2011/0104770 A1 | 5/2011 | Tobey |
| 2011/0300593 A1 | 12/2011 | Mihalcea et al. |

FOREIGN PATENT DOCUMENTS

WO    2011163373    12/2011

OTHER PUBLICATIONS

PCT (PCT/US20131078200) Notification of Transmittal of the International Search Report and Written Opinion of the International Searching Authority, Mailed Apr. 22, 2014, 12 pages.

*Primary Examiner* — Karen Cochrane Carlson
*Assistant Examiner* — Jennifer M. H. Tichy

(57) ABSTRACT

High conversion efficiency processes are disclosed for the anaerobic bioconversion of syngas to alcohol by microorganisms having metabolic processes that utilize sulfur in limited amounts. The processes remove hydrogen sulfide from the gas leaving the bioreactor assembly by forming sulfur compounds that are beneficial to the microorganisms. The sulfur compounds can be returned to the bioreactor assembly to meet a portion of microorganism sulfur demand.

17 Claims, 2 Drawing Sheets

SULFUR MANAGEMENT FOR PROCESSES AND CONTROL SYSTEMS FOR THE EFFICIENT ANAEROBIC CONVERSION OF HYDROGEN AND CARBON OXIDES TO ALCOHOLS

FIELD OF THE INVENTION

This invention pertains to processes for recovering byproduct hydrogen sulfide for use in systems for anaerobic conversion of hydrogen and carbon oxides to alcohols especially ethanol, propanol and butanol.

BACKGROUND

Anaerobic fermentations of hydrogen and carbon monoxide involve the contact of the substrate gas in an aqueous fermentation broth with microorganisms capable of generating alcohols such as ethanol, propanol, i-butanol and n-butanol. The production of these alcohols requires significant amounts of hydrogen and carbon monoxide. For instance, the theoretical equations for the conversion of carbon monoxide and hydrogen to ethanol are:

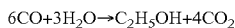

$6CO + 3H_2O \rightarrow C_2H_5OH + 4CO_2$

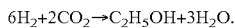

$6H_2 + 2CO_2 \rightarrow C_2H_5OH + 3H_2O$.

As can be seen, the conversion of carbon monoxide results in the generation of carbon dioxide. The conversion of hydrogen involves the consumption of hydrogen and carbon dioxide, and this conversion is sometimes referred to as the $H_2/CO_2$ conversion. For purposes herein, it is referred to as the hydrogen conversion.

Typically the substrate gas for carbon monoxide and hydrogen conversions is, or is derived from, a synthesis gas (syngas) from the gasification of carbonaceous materials, from partial oxidation or reforming of natural gas and/or biogas from anaerobic digestion or landfill gas or off-gas streams of various industrial methods such as off gas from coal coking and steel manufacture. The substrate gas contains carbon monoxide, hydrogen, and carbon dioxide and usually contains other components such as water vapor, nitrogen, methane, ammonia, hydrogen sulfide, and the like.

These substrate gases are typically more expensive than equivalent heat content amounts of fossil fuels. Hence, a desire exists to use these gases efficiently to make higher value products. The financial viability of any conversion process, especially to commodity chemicals such as ethanol, will depend, in part, upon the costs of the feedstocks, conversion efficiency and operating and capital costs for generating the substrate gases; and upon the capital costs, the efficiency of conversion of the carbon monoxide and hydrogen to the sought products and the energy costs to effect the conversion of the substrate gases to the higher value products.

In a bioreactor, hydrogen and carbon oxides pass from the gas phase to being dissolved in the aqueous broth, and then the dissolved hydrogen and carbon oxides contact the microorganisms for bioconversion. Due to the low solubilities of carbon monoxide and, especially, hydrogen in aqueous media, mass transfer can be a limiting factor rate and conversion in the bioconversion to alcohol. Therefore challenges exist in the design of commercial scale bioreactors that provide for the sought mass transfer while still enabling a high conversion of gas substrate at capital and operating costs that enable such a facility to be commercially competitive.

The off gases from bioreactors contain substrate that was not bioconverted and diluents such as methane, carbon dioxide, nitrogen, hydrogen sulfide, and other impurities. Also, the microorganisms present in the bioreactor metabolize components to impurities such as hydrogen sulfide, oxygen, nitrogen, hydrogen and other gases. The byproduct off gas can be combusted to produce heat and electricity, but this is not without concern. Specifically, hydrogen sulfide is toxic and if released to the atmosphere has a propensity to produce acid rain. Upon combustion of the raw off gas, the hydrogen sulfide present will form sulfur oxides, which are stack gas pollutants. Environmental regulations typically require removal and disposal of such stack gas pollutants. Commercial processes for removing sulfur before or after combustion are known; however, the treating of sulfur containing gas and sulfur recovery have significant cost and operating disadvantages that can impact commercial viability. Also, while various processes for sulfide recovery via alkali, for example sodium hydroxide, calcium hydroxide, and so forth, are known, the acidic nature of the off gas due to the co-produced carbon dioxide would result in excessive alkali consumption. More specifically, a lower and more acidic pKal of 6.37 for carbon dioxide compared to a pKal of 7.04 for hydrogen sulfide means increased alkali consumption to recover sulfide from the carbon dioxide containing bioreactor off gas. Accordingly, the costs associated with the equipment and its operation to recover sulfide by treating bioreactor off gas with alkali can make such recovery impractical.

Sulfur compounds, such as but not necessarily limited to, hydrogen sulfide, bisulfite, thiosulfate, and so forth, play a complex role in bioreactors and the effect on the microorganisms used in the anaerobic fermentation of hydrogen and carbon monoxide. The microorganisms that bring about such anaerobic fermentation generate very little metabolic energy, and do require some sulfur to maintain biological activity. Consequently, the relatively slow growth of the microorganisms, which often continue substrate fermentation during the non-growth phase of their life cycle to gain metabolic energy for their maintenance, can depend on available sulfur. While sustaining the microorganisms requires a certain presence of sulfur in the bioreactor feed, sulfur too much in excess of microorganism needs may be detrimental to microorganism activity for the anaerobic fermentation of hydrogen and carbon monoxide to liquid products.

Although known processing steps exist to remove hydrogen sulfide from bioreactor off gas to produce sulfide, large chemical consumption, particularly alkali, detracts from the commercial viability of the disclosed process.

Processes are therefore sought that can provide removal and conversion of off gas hydrogen sulfide to sulfur compounds that can be fed to the bioreactor to meet microorganism sulfur demand. Desirably such processes can operate at atmospheric pressure and low temperatures without the excessive cost of expensive chemicals and operate without the generation of hazardous and/or toxic wastes.

SUMMARY

By this invention continuous processes are provided for the anaerobic conversion of hydrogen and carbon oxides to higher alcohols, especially ethanol, propanol and butanol. Further, the processes produce off gas from the bioreactors that is characterized as comprising hydrogen sulfide along with other gaseous components. Thus, the removal and conversion of hydrogen sulfide from the off gas to form sulfur compounds that are useful to the microorganisms in the bioreactors can be used to advantage.

In the processes of this invention, hydrogen sulfide is removed from the bioreactor off gas by contacting the off gas with an aqueous sulfite solution so as to produce sulfur compounds that are useful in meeting microorganism sulfur needs. Moreover, the processes of this invention directly recycle the sulfur compounds to the bioreactor feed so as to minimize byproduct sulfur removal and disposal.

In a broad fermentation aspect this invention pertains to continuous process for the anaerobic bioconversion of a gas substrate comprising at least one of carbon monoxide and hydrogen with carbon dioxide in an aqueous broth containing microorganisms, the microorganisms having metabolic processes that utilize sulfur in limited amounts, suitable for converting said substrate to alcohol comprising:

a. continuously introducing said gas substrate into a bioreactor assembly having at least one bioreactor for containing said broth, said bioreactor having at least one gas inlet for introducing said substrate gas at least one gas outlet;

b. maintaining contact of the microorganisms with the gas substrate and said broth to provide an alcohol-containing broth and a substrate depleted gas phase at the at least one gas outlet of said bioreactor assembly, said duration of contact being sufficient to convert at least about 80 or 85, preferably at least about 90, percent of the hydrogen and at least about 98, preferably at least about 99, percent of any carbon monoxide in the gas substrate to alcohol;

c. continuously or intermittently withdrawing a portion of said broth from said bioreactor assembly for recovery of said alcohol, said withdrawal being sufficient to maintain the alcohol in said broth below a concentration that unduly adversely affects the microorganisms;

d. continuously withdrawing the substrate depleted gas phase from said bioreactor assembly at said at least one gas outlet wherein the substrate depleted gas phase being withdrawn from the bioreactor assembly contains hydrogen sulfide;

e. converting, reacting, and/or removing at least a portion of the hydrogen sulfide from the substrate depleted gas phase to form sulfur compounds that include sulfur compounds that are beneficial to microorganisms in the bioreactor; and, f. introducing at least a portion of the sulfur compounds to at least one or more inlets of a bioreactor assembly.

Where substrate is provided to the bioreactor assembly via more than one gas inlets, the composition of the substrate feed may be the same or different at each gas inlet. Overall or cumulative gas substrate means the total exogenous gas substrate introduced to the bioreactor assembly through all gas inlets of the bioreactors. Such overall gas substrate, for instance, if more than one bioreactor is used, can have a portion of the substrate, which may have the same or different composition as that fed to the prior bioreactor, may be added to the off gas from one stage and the combined gases passed to the subsequent stage. It is also possible to add a portion of the substrate at different locations in the height of the bioreactor. Similarly, sulfur recovered from the depleted substrate in the form of various sulfur compounds can be provided to the bioreactor assembly via more than one feed inlets either at the same elevation or different elevations.

In another broad aspect of this invention, processes are provided for controlling the operation of a bioreactor assembly for the anaerobic bioconversion of a gas substrate comprising at least one of carbon monoxide and hydrogen with carbon dioxide in an aqueous broth containing microorganisms, the microorganisms having metabolic processes that utilize sulfur in limited amounts, suitable for converting said substrate to alcohol wherein:

a. the gas substrate is continuously introduced in the form of gas bubbles at one or more gas inlets of a bioreactor assembly having at least one bioreactor for containing said broth, said bioreactor having at least one gas inlet for introducing said substrate gas, at least one gas outlet and at least one bioreactor characterized as having a substantially uniform aqueous broth and a substantially non-uniform substrate concentration between the gas inlet and the gas outlet;

b. contact is maintained between the gas substrate and the broth to provide an alcohol-containing broth and a substrate depleted gas phase at a gas outlet portion of the bioreactor assembly;

c. substrate depleted gas phase, which contains hydrogen sulfide, is continuously withdrawn from said bioreactor assembly at the at least one gas outlet;

d. a portion of said broth is continuously or intermittently withdrawn from said bioreactor assembly for recovery of said alcohol, said withdrawal being sufficient to maintain the alcohol in said broth below a concentration that unduly adversely affects the microorganisms;

e. at least a portion of the hydrogen sulfide from the depleted gas phase is converted, reacted, and/or removed with a sulfur additive and forms sulfur compounds which are beneficial to microorganisms in the bioreactor; and, f. a portion of the sulfur compounds is introduced to at least one or more inlets of a bioreactor assembly, with the process further comprising adjusting a rate of introduction of the sulfur compounds to the at least one or more inlets of a bioreactor assembly, and adjusting the carbon dioxide concentration in the gas substrate to provide a partial pressure of carbon dioxide in the substrate depleted gas phase at the at least one gas outlet to be in the range of about 2.5 and 30 or 40, preferably between about 3.5 and 10 or 20, kPa.

The beneficial sulfur compounds may be obtained in any convenient manner from the hydrogen sulfide in the bioreactor off gas and its reaction with a sulfur additive. Usually the sulfur compounds result from contacting the depleted gas substrate with an aqueous sulfite solution, which is preferably made from sodium sulfite.

The preferred processes of this invention exhibit a high conversion efficiency of carbon to alcohol. On a total carbonaceous feedstock, including feedstock used to provide heat energy to the process for generating the syngas, the conversion efficiency is often at least about 50, preferably at least about 60, and more preferably at least about 65, atomic percent of the feedstock introduced is converted to alcohol.

In another broad aspect, this invention pertains to continuous processes for the anaerobic bioconversion of a syngas comprising carbon monoxide and hydrogen, together with carbon dioxide and/or nitrogen in an aqueous broth containing microorganisms, the microorganisms having metabolic processes that utilize sulfur in limited amounts, suitable for converting said substrate to alcohol comprising:

a. continuously reforming a hydrocarbonaceous feedstock to produce syngas;

b. continuously introducing said syngas in the form of gas bubbles at one or more gas inlets of a bioreactor assembly having at least one bioreactor for containing said broth, said bioreactor having at least one gas inlet, for introducing said substrate gas, at least one gas outlet, and at least one bioreactor in the bioreactor assembly is characterized as having a substantially uniform aqueous broth and a substantially non-uniform substrate concentration between the gas inlet and the gas outlet;

b. maintaining contact between the gas bubbles and said broth to provide an alcohol-containing broth and a syngas depleted gas phase at a gas outlet of said bioreactor assembly, said duration of contact being sufficient to convert at least about 90 percent of the hydrogen and at least about 98 percent of the carbon monoxide in the gas substrate to alcohol;

c. continuously withdrawing syngas depleted gas phase from said bioreactor assembly at said at least one gas outlet wherein the syngas depleted gas phase being withdrawn from the bioreactor assembly contains hydrogen sulfide and has a partial pressure of carbon dioxide in the range of about 2.5 and 40 kPa;

d. continuously or intermittently withdrawing a portion of said broth from said bioreactor assembly for recovery of said alcohol, said withdrawal being sufficient to maintain the alcohol in said broth below a concentration that unduly adversely affects the microorganisms;

e. passing at least of portion of the depleted gas stream through a vapor-liquid contacting device and passing at least one of bisulfite or a bisulfite compound to the vapor-liquid contacting zone to produce thiosulfate; and, f. passing at least a portion of the thiosulfate to the fermentation zone.

The partial pressure of carbon dioxide in the syngas depleted gas phase is maintained between about 2.5 and 40 kPa both the rate of bioconversion of hydrogen to ethanol and the driving force for mass transfer of hydrogen from the gas to aqueous phase operate together to achieve the high conversion of hydrogen. Thus, with the high conversion of hydrogen and carbon monoxide, the residual energy in the syngas depleted gas phase is at a level where capture of that energy is not essential to provide a high efficiency of conversion of feedstock to alcohol.

While the process of this invention is highly useful for the fermentation processes as described it can also find utility in other process and in particular industrial applications. In particular, regulations often impose significant clean up burden on facilities that generate a combined $H_2S$ in quantities of more than 190 lbs/day (equivalent to 100 tons/year of $SO_x$. The processes of this invention could greatly reduce such the requirement for effluent gas treatment for the waste gases gas produced by facilities that individually or collectively produce syngas in such high amounts.

DETAILED DISCUSSION

Definitions

Figure 1:
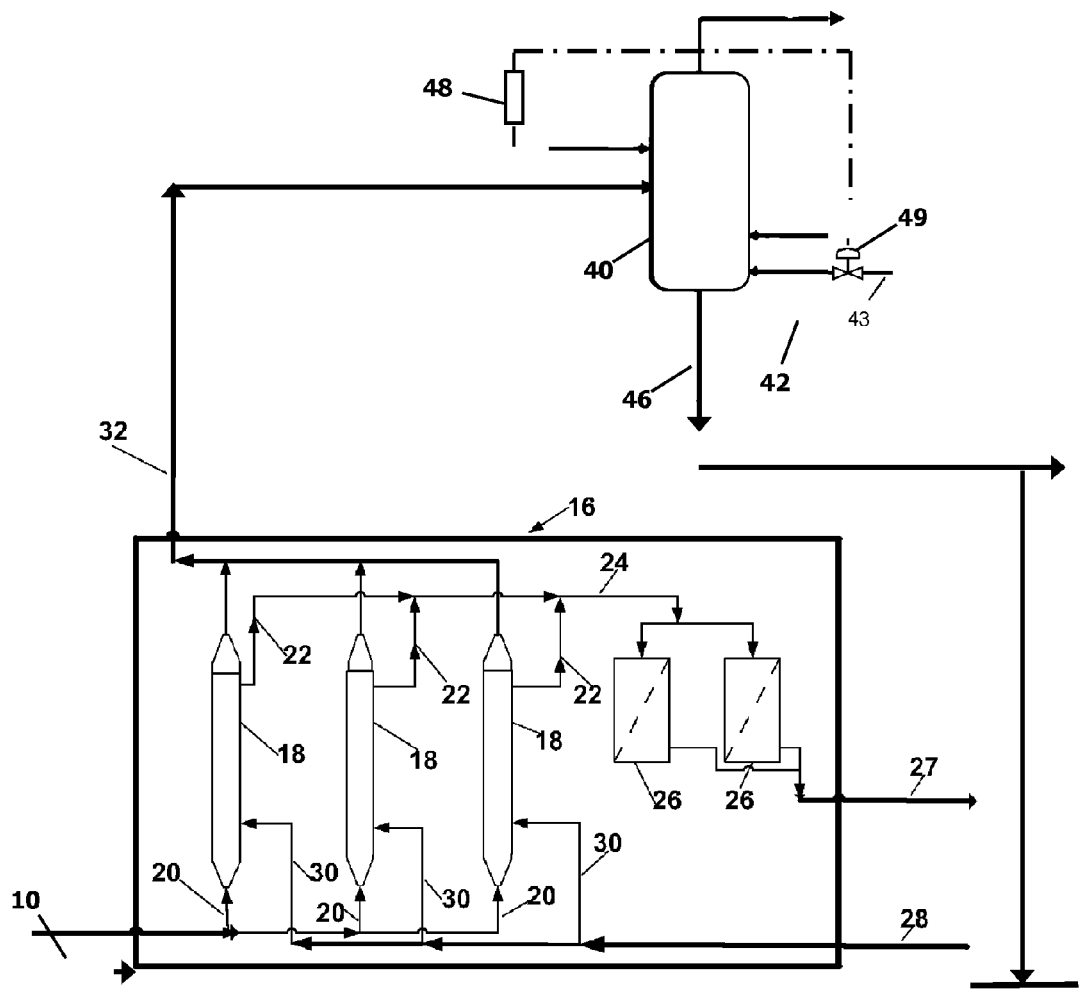
FIG. 1 is a schematic depiction of an apparatus suitable for practicing the processes of this invention.

Alcohol means one or more alkanols containing two to six carbon atoms. In some instances alcohol is a mixture of alkanols produced by the microorganisms contained in the aqueous broth.

Biomass means biological material living or recently living plants and animals and contains at least hydrogen, oxygen and carbon. Biomass typically also contains nitrogen, phosphorus, sulfur, sodium and potassium. The chemical composition of biomass can vary from source to source and even within a source. Sources of biomass include, but are not limited to, harvested plants such as wood, grass clippings and yard waste, switchgrass, corn (including corn stover), hemp, sorghum, sugarcane (including bagas), and the like; and waste such as garbage and municipal waste. Biomass does not include fossil fuels such as coal, natural gas, and petroleum.

The term bioreactor off gas means either the substrate depleted or syngas depleted gas phase from the bioreactor assembly.

The term Component Composition means the composition of a gas where both water and nitrogen have been excluded from the calculation of the concentration of the components. As used herein, unless otherwise stated, compositions of gases are on an anhydrous basis and exclude the presence of nitrogen.

Electron to carbon ratio is calculated as the quotient of the quantity of two times the sum of the concentrations of carbon monoxide and hydrogen divided by quantity of the sum of the concentrations of carbon monoxide and carbon dioxide:

$$e^-/C = 2([CO]+[H_2])/([CO]+[CO_2]).$$

The abbreviation ppm means parts per million. Unless otherwise stated or clear from the context, ppm is on a mole basis (ppm (mole)).

Aqueous broth, or aqueous fermentation broth, means a liquid water phase which may contain dissolved compounds including, but not limited to hydrogen, carbon monoxide, and carbon dioxide.

Intermittently means from time to time and may be at regular or irregular time intervals.

A concentration of alcohol or sulfur below that which unduly adversely affects the rate of growth of the culture of microorganisms will depend upon the type of microorganism and the alcohol or sulfur species. An unduly adverse effect on the growth rate means that a significant, usually at least a 20 percent, decrease in the growth rate of the microorganisms is observed in comparison to the growth rate observed in an aqueous broth having about 10 grams per liter alcohol therein, all other parameters being substantially the same.

Syngas means a gas containing at least one of hydrogen and carbon monoxide and may, and usually does, contain carbon dioxide.

Overview

The processes of this invention provide for high anaerobic bioconversion efficiencies of syngas to alcohol. These efficiencies of the processes are achieved at least in part by the use of by product such as hydrogen sulfide in the bioreactors off gas to produce sulfur compounds useful to microorganisms in the bioreactors. The processes also remove bioreactor off gas hydrogen sulfide in an environmental and economical manner.

Syngas Generation

The source of the syngas is not critical to the broad aspects of this invention. Gasification, partial oxidation, and reforming (autothermal and steam) of biomass or fossil carbonaceous materials can be used. Gasification and partial oxidation processes are disclosed in copending U.S. patent application Ser. No. 13/304,902, filed on Nov. 28, 2011, hereby incorporated by reference in its entirety. Rice, et al, in "Autothermal Reforming of Natural Gas to Synthesis Gas", Reference: KBR Paper #2031, Sandia National Laboratories, April 2007, discuss autothermal reforming and conditions. Steam reforming is a widely practiced commercial unit operation. See Logdberg, et al., "Natural Gas Conversion", Haldor Topsoe publication (undated). Reforming in the presence of carbon dioxide is known as carbon dioxide reforming with the partial pressure of carbon dioxide causing a shift in the product distribution of the reforming. See, for instance, Madsen, et al, "Industrial Aspects of $CO_2$-reforming", Paper No. 28f, presented at the AIChE Spring Meeting, Houston, Tex., March 1997. Reforming is a temperature dependent equilibrium reaction, and thus the addition of hydrogen, carbon monoxide or carbon dioxide will affect the distribution of steam, hydrogen, carbon monoxide and carbon dioxide from the fresh feed although the distribution in the produced syngas will be set by the thermodynamic equilibria. For example, natural gas having its sulfur content reduced is passed to a steam reformer which converts the hydrocarbons in the natural gas to a syngas containing hydrogen, carbon monoxide and carbon dioxide. Lower pressure steam reformer operation provides less methane breakthrough then at higher pressure operations such that the syngas contains about 75 mole percent hydrogen, about 18 mole percent carbon monoxide, about 5.5 mole percent carbon dioxide, and about 1.5 mole percent methane on an anhydrous basis.

Where a source of carbon dioxide is available, steam reforming is generally preferred due to the high hydrogen concentration of the produced syngas and the relative absence of contaminants that must be removed to prevent deleterious effects on the microorganisms for the anaerobic bioconversion to alcohol. Additionally, steam reforming, being non-oxidative, provides a syngas that is relatively free of nitrogen which would be present in the syngas produced by a partial oxidation or autothermal reforming process using air or enriched air as the oxygen source. Another advantage of steam reforming is that the depleted gas phase from the bioreactors can be used as a portion of the fuel required for providing the heat for the steam reforming. By using the depleted gas phase to provide heat, and offset of fresh carbonaceous feed occurs and thereby enhances the net conversion of fresh carbonaceous feed to alcohol. The portion of the carbonaceous feed that can be offset will depend upon the volume and heating value of the depleted gas phase, and related hydrogen sulfide removal, processing, and utilization efficiencies.

An advantage of autothermal reforming is that operating conditions can be selected to provide a syngas having the sought electron to carbon atom ratio. The electron to carbon ratio can be adjusted by operational variables for autothermal reforming. For instance, increasing the preheat temperature of the feed to the autothermal reforming enables a reduction in the amount of combustion required during the autothermal reforming to provide the sought temperature. Thus the concentration of carbon dioxide in the syngas is reduced. The steam to hydrocarbonaceous feed ratio can also be adjusted to provide the sought electron to carbon ratio with higher steam ratios increasing the electron to carbon ratio. Since the processes of this invention enable a high conversion of hydrogen to alcohol, advantageous processes can be provided where air or oxygen-enriched air is used as the oxygen source for the autothermal reforming. Although the nitrogen diluent may reduce the energy density of the substrate depleted gas phase from the bioreactor assembly and render it less useful or without utility as a gas for combustion to provide heat, e.g., for a steam boiler, high feedstock to alcohol conversions can still be achieved.

Since the unit operations to make the syngas can vary widely, it is understood that the compositions of the syngas may similarly vary widely including the presence of components other than hydrogen, carbon monoxide and carbon dioxide, which components may be inert such as nitrogen and methane or components that may have to be removed due to potential adverse effects on the microorganisms such as hydrogen cyanide. Processes for removing adverse components include those disclosed in U.S. patent application Ser. No. 13/304,902, filed on Nov. 28, 2011; Ser. No. 13/440,953, filed on Apr. 5, 2012; and Ser. No. 13/525,079, filed on Jun. 15, 2012; and U.S. Pat. No. 7,927,513 filed on Oct. 27, 2009 and U.S. Pat. No. 8,303,849, filed on Nov. 9, 2010, all hereby incorporated by reference in their entireties. Also, the hydrogen sulfide content of the substrate depleted gas phase from the bioreactor assembly may vary widely. An advantage of the control system of the processes of this invention is that such variations in the hydrogen sulfide content of the substrate depleted gas phase from the bioreactor assembly can be accommodated to provide a solution having sulfur compounds produced by removing the hydrogen sulfide to the bioreactor assembly that enables achieving a high conversion of hydrogen and carbon monoxide to alcohol.

In some instances, more than one source of syngas may be used, and it may be desired to use different types of unit operations, e.g., a steam reformer and an autothermal reformer or partial oxidation unit or gasifier, to produce syngas so as to provide the desired overall substrate gas composition.

Alcohol, Microorganisms and Fermentation Conditions

The alcohol or alcohols produced in the processes of this invention will depend upon the microorganism used for the fermentation and the conditions of the fermentation. One or more microorganisms may be used in the fermentation broth to produce the sought alcohols. Bioconversions of CO and $H_2/CO_2$ to propanol, butanol, ethanol and other alcohols are well known. For example, in a recent book concise description of biochemical pathways and energetics of such bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Bacteria, L. G. Ljungdahl eds., Springer (2003). Any suitable microorganisms that have the ability to convert the syngas components: CO, $H_2$, $CO_2$ individually or in combination with each other or with other components that are typically present in syngas may be utilized. Suitable microorganisms and/or growth conditions may include those disclosed in U.S. patent application Ser. No. 11/441,392, filed May 25, 2006, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; U.S. Pat. No. 7,704,723 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include: *Clostridium Ljungdahlii*, with strains having the identifying characteristics of ATCC 49587 (U.S. Pat. No. 5,173,429) and ATCC 55988 and 55989 (U.S. Pat. No. 6,136,577) that will enable the production of ethanol as well as acetic acid; *Clostridium autoethanogenum* sp. nov., an anaerobic bacterium that produces ethanol from carbon monoxide. Jamal Abrini, Henry Naveau, Edmond-Jacques Nyns, Arch Microbiol., 1994, 345-351; Archives of Microbiology 1994, 161: 345-351; and *Clostridium Coskatii* having the identifying characteristics of ATCC No. PTA-10522 U.S. Pat. No. 8,143,037, filed on Mar. 19, 2010. All of these references are incorporated herein in their entirety.

Suitable microorganisms for bioconversion of syngas to alcohol generally live and grow under anaerobic conditions, meaning that dissolved oxygen is essentially absent from the fermentation liquid. Adjuvants to the aqueous broth may comprise buffering agents, trace metals, vitamins, salts, sulfur compounds, etc. Adjustments in the broth may induce different conditions at different times such as growth and non-growth conditions which will affect the productivity of the microorganisms. U.S. Pat. No. 7,704,723, hereby incorporated by reference in its entirety, discloses the conditions and contents of suitable aqueous broth for bioconversion CO and $H_2/CO_2$ using anaerobic microorganisms.

The biological conversion of syngas to alcohols, including but not necessarily limited to ethanol, propanol, propionic acid, butanol, and so forth, is a process that requires microorganisms that must maintain metabolic activity by biological processes that consume certain types of amino acids. Amino acids useful to microorganisms to maintain biological activity include sulfur containing amino acids, such as methionine, cysteine, and/or cystine. In bioreactor systems for the production of alcohols such as ethanol from syngas, sulfur containing amino acids can be supplied to meet microorganism sulfur demand needed to maintain metabolic activity. Alternately, sulfur compounds, such as hydrogen sulfide, bisulfite, and so forth, can be provided to the microorganisms, which in turn convert these sulfur compounds to the required sulfur containing compounds needed to maintain metabolic activity. Further, additives, such as, but not necessarily limited to, sulfite, bisulfite, and metabisulfite can be usefully employed for the conversion of hydrogen sulfide to sulfur compounds which are beneficial to the microorganisms. Thus, as the microorganisms consume sulfur containing amino acids, the consumed amino acids can be replaced either directly or produced by the microorganism from sulfur compounds, such as hydrogen sulfide, bisulfite, and so forth, that are in the bioreactor feed. In a particular embodiment sulfur is present in the fermentation medium at a concentration of at least 0.1, typically in a range of 0.1 to 10 and preferably in a range of 0.5 to 2 mmol sulfur per gram dry cell weight of microorganism.

Anaerobic fermentation conditions include a suitable temperature, say, between 25° and 60° C., frequently in the range of about 30° to 40° C. The conditions of fermentation, including the density of microorganisms, aqueous broth composition, and syngas residence time, are preferably sufficient to achieve the sought conversion efficiency of hydrogen and carbon monoxide and will vary depending upon the design of the fermentation reactor and its operation. When using the additives of this invention, the pH in the fermentation zone is usually kept below 5.3 preferably below 4.9, and typically in a range of 4.3 to 5.1 The pressure may be subatmospheric, atmospheric or super atmospheric, and is usually in the range of from about 90 to 1000 KPa absolute and in some instances higher pressures may be desirable for biofilm fermentation bioreactors. As most bioreactor designs, especially for commercial scale operations, provide for a significant height of aqueous broth for the fermentation, the pressure will vary within the fermentation bioreactor based upon the static head. The fermentation conditions are preferably sufficient to effect at least about 85, preferably at least about 90, percent of the hydrogen in the substrate gas fed to the bioreactor assembly to alcohol.

The instant invention can use any type of bioreactor to retain the microorganisms for the conversion of the syngas. Many devices and equipment are used for gas transfer to microorganisms in fermentation and waste treatment applications. Conventional systems will retain a substantial volume of fermentation liquid in a vessel or column and use means for agitation to promote mass transfer between the relatively insoluble syngas components and the microorganisms retained in the fermentation liquid. In application of this invention to the production of liquid products from gas streams, in particular CO or a mixture of CO2 and H2, the liquid column will typically comprise a bioreactor that retains microorganisms suspended in a fermentation liquid.

Specific types of bioreactors include bubble column bioreactors and stirred tank bioreactors. For these types of bioreactors, the fermentation zone, sometimes referred to as a planktonic fermentation zone, injects the substrate gas into a large volume of fermentation broth. This type of fermentation zone may take many different forms such as a continuously stirred tank reactor (CSTR), gas lift or fluidized beds, and the circulation of liquids or gases via contacting devices. In a preferred form of this invention the fermentation zone is a bubble column bioreactor (BCBR). These conventional bioreactors and systems may use agitators with specialized blades or configurations to create a continuous stirred reactor. The fluidized systems are generally configured for use with microorganisms in planktonic form, i.e. the microorganisms exist as individual cells in liquid medium. Gas dissolution rates for such systems are also generally low.

Cell retention by formation of biofilms is a very good and often inexpensive way to increase the density of microorganisms in bioreactors. This requires a solid matrix with large surface area for the cells to colonize and form a biofilm that contains the metabolizing cells in a matrix of biopolymers that the cells generate. Trickle bed and some fluidized bed bioreactors make use of biofilms to retain microbial cells on solid surfaces while providing dissolved gases in the liquid by flow past the solid matrix. Such bioreactors suffer from either being very large or unable to provide sufficient gas dissolution rates.

The use of bioreactors that retain biofilms has been proposed for the production of liquid fuels. US Applications 20080305539 and 2009029434 show the use of a bioreactor to support microorganisms on or in a membrane (preferably hollow fiber membranes) for the production of ethanol from syngas. US Application 20090035848 shows the use of bioreactor for producing ethanol from syngas using microorganisms retained on media that circulates as a moving bed in a fermentation liquid. In both of these bioreactors, the fermentation liquid retains the ethanol from the microorganisms in dilute concentration.

Looking again at the preferred BCBR fermentation zone, a BCBR injects the gas substrate in the form of bubbles that create a mixing action of the broth as the bubbles flow upward and the substrate is absorbed by the liquid, is consumed by the microorganisms, and the gas substrate gets replaced by the off gas of the fermenter. A combination of bubble size and duration of contact with the aqueous fermentation broth are necessary to achieve these high conversions in a BCBR type fermenter All these systems for conversion of biomass derived syngas rely on a fermentation broth that provides a low concentration of ethanol in a relatively large volume of aqueous liquid. Ethanol concentration will ordinarily fall below 6% and in most cases less than 4%. As a result practical recovery of ethanol from the fermentation broth requires a separation system that can efficiently recover the ethanol from the dilute fermentation liquid.

For commercial operations, the fermentation operation preferably provides a total molar conversion of hydrogen and carbon monoxide in the substrate gas feed in the range of at least about 93, preferably at least about 97, mole percent. If required to provide adequate contact time between the gas bubbles and the aqueous fermentation broth, more than one bioreactor may be used in gas flow series in the bioreactor assembly. The use of sequential, deep tank bubble column bioreactors is disclosed in U.S. patent application Ser. No. 13/243,062, filed on Sep. 23, 2011, herein incorporated by reference in its entirety.

The rate of supply of the gas feed under steady state conditions to a fermentation bioreactor is preferably such that the rate of transfer of carbon monoxide and hydrogen to the liquid phase matches the rate that carbon monoxide and hydrogen are bioconverted. The rate at which carbon monoxide and hydrogen can be consumed will be affected by the nature of the microorganism, the concentration of the microorganism in the aqueous broth and the fermentation conditions. As the rate of transfer of carbon monoxide and hydrogen to the aqueous broth is a parameter for operation, conditions affecting the rate of transfer such as interfacial surface area between the gas and liquid phases and driving forces are important.

Preferably the substrate gas is introduced into the BCBR in the form of microbubbles. Often the microbubbles have diameters in the range of 0.01 to 0.5, preferably 0.02 to 0.3 millimeter. Preferably the substrate gas is injected using a motive fluid. Variations in the motive liquid flow rate can be used to modulate the microbubble size and thus modulate the rate of transfer of carbon monoxide and hydrogen to the liquid phase. Moreover, the modulation provides microbubbles that provide a stable gas-in-liquid dispersion. The injectors may be jet mixers/aerators or slot injectors. Slot injectors are preferred, one form of which is disclosed in U.S. Pat. No. 4,162,970. These injectors operate using a motive liquid. The injectors, especially slot injectors, are capable of operating over a wide range of liquid and gas flow rates and thus are capable of significant turn down in gas transfer capability. The injectors are characterized as having nozzles of at least about 1, often about 1.5 to 5, say, 2 to 4, centimeters as the cross-sectional dimension in the case of jet injectors or as the smaller cross-sectional dimension in the case of slot injectors. The bubble size generated by the injectors will be influenced by, among other factors, the rate of liquid flow through the injector and the ratio of gas phase to liquid phase passing through the injector as well as characteristics of the aqueous broth itself including, but not limited to its static liquid depth. (See also, U.S. patent application Ser. No. 13/243,062, filed on Sep. 23, 2011.) In some instances the microbubbles, which form a less dense gas-liquid dispersion, and any motive fluid used to generate the microbubbles, can facilitate liquid mixing in a bioreactor.

Substrate Depleted Gas Phase

The bioreactor off gas is a substrate depleted gas phase egressing from the fermentation zone that contains a small fraction of the hydrogen and carbon oxides introduced into the bioreactor assembly as the substrate gas. Inerts such as nitrogen and primarily methane will comprise a portion of the depleted gas phase where syngas from steam reforming or oxygen fed autothermal reforming is used. Thus the depleted gas phase has heating value when combusted or can be recycled, at least in part, to the unit operation used for producing the syngas or to a steam boiler or the like. The carbon dioxide content of the substrate depleted gas phase is sufficiently low that it may be recycled as feed to the unit operation used for producing the syngas without unduly affecting the composition of the reformate. Hence, high methane-content substrate depleted gases could be admixed with feedstock to a reformer, especially prior to the sulfur remove unit operation of the reformer. The depleted gas phase may also contain sulfur-containing compounds, alcohol and the like volatilized from the aqueous fermentation broth.

Other contaminants in the depleted gas phase from the bioreactor will include hydrogen sulfide. Typically, the bioreactor off gas contains 10 to 150 ppm hydrogen sulfide. The corresponding sulfur contained in the bioreactor off gas represents an estimated amount of between about 10 to about 30 percent, and more often 20 to 30 percent, of the bioreactor microorganism sulfur demand needed to maintain metabolic activity. An aqueous sulfite solution can be used to capture hydrogen sulfide from the bioreactor off gas to produce sulfur compounds useful to the microorganism in the bioreactors. The overall chemistry is shown by the following equations.

While the above reaction generally represents overall stoichiometry, the detailed reaction mechanism is very complicated and involves numerous reactions of sulfur, sulfite, bisulfite, thiosulfate, tetrathionate, pentathinate, and so forth. Further, sulfur and sulfides will naturally disproportionate with sulfite to produce thiosulfate, which is available as a sulfur source to sulfur consuming microorganisms. In any case, such chemical systems remove hydrogen sulfide from the off gas so as to produce an aqueous solution having sulfur compounds that are useful to the microorganisms in the bioreactors. The particular additives for conversion of the hydrogen sulfide include sulfite, bisulfite, and metabisulfite. The additive may be derived by the addition of various metabisulfite salts that include sodium bisulfite, sodium metabisulfite, and potassium metabisulfite. An important sulfur compound property is substantial solubility in the fermentation broth. For example, metabisulfite and bisulfite exist in equilibrium in water. Fazio T. and C. R. Warner. 1990. A Review of Sulphites in Foods: analytical methodology and findings. Food Addit. Contam. 7:433-454. In particular embodiments, the sulfur additive is a solution of a bisulfite compound such as sodium bisulfite obtained in preferred form as 5 molar bisulfite solution and diluted to provide a stock solution at a preferred concentration from of about 1.2 mM. The concentration of bisulfite in solution will depend on various factors including pH and solubility.

Useful and non-limiting examples of systems for contacting the bioreactor off gas with aqueous solutions include spray towers, packed towers, scrubbers such as venturi scrubbers, and so forth. Also, hydrogen sulfide removal from the bioreactor off gas can be adjusted to remove enough hydrogen sulfide such that the resulting off gas can be combusted without the need of further sulfur clean up. In the cases where a bioreactor assembly already uses an off gas vapor-liquid contacting device no extra equipment or unit operations need be added to the bioreactor assembly to use this invention.

Product Recovery

The fermentation vessel may have added from time to time or continuously one or more streams of water, nutrients or adjuvants, and microorganisms. A portion of the aqueous broth is withdrawn from time to time or continuously from the bioreactor for product recovery. Usually, the withdrawal is made at a point at the upper portion of the aqueous broth in the vessel. Product recovery can consist of known equipment arrangements for removal of residual cell material, separation and recovery of liquid products from the fermentation liquid, return of recovered fermentation liquid and purging of waste streams and materials. Suitable equipment arrangements can include filters, centrifuges, cyclones, distillation columns, membrane systems and other separation equipment. U.S. Pat. No. 8,211,679, herein incorporated by reference in its entirety, shows an arrangement for a product recovery bioreactor that recovers an ethanol product from a bioreactor.

DRAWINGS

A general understanding of the invention and its application may be facilitated by reference to FIG. 1. The Figure is not in limitation of the broad aspects of the invention.

FIG. 1 is a schematic depiction of an apparatus generally suitable for practicing the processes of this invention. FIG. 1 omits equipment such as pumps, compressors, valves, instruments and other devices the placement of which and operation thereof are well known to those practiced in chemical engineering. FIG. 1 also omits ancillary unit operations. The process and operation of FIG. 1 will be described in the context of the recovery and processing of the substrate depleted gas from the bioreactors, the bioreactor off gas. The process is readily adaptable to making generally alcohols via a bioconversion process as described herein.

For purposes of discussion, the syngas is produced from natural gas. As generally known in the industry, any sulfur in the natural gas is removed before the natural gas is converted to a syngas containing hydrogen, carbon monoxide and carbon dioxide and other minor amounts of other gases. It should be recognized that other carbonaceous sources can be used to provide syngas. The primary conversion processes include steam reforming but other syngas producing operations can be used such as gasification, partial oxidation and autothermal reforming.

The major gas components of the fresh, clean syngas are consumed in the bioreactors to produce liquid fuel components; however, sulfur compounds, as described above, useful to the bioreactor microorganisms are also fed to bioreactors to maintain microorganism metabolic activity. A stream of clean syngas enters the process via a line 10 and enters a membrane type bioreactor (MSBR) section 16. Line 10 feeds the syngas stream to a trio of membrane bioreactors 18 in series via distribution lines 20. The syngas contacts the fermentation liquid in the bioreactors 18 and the microorganisms consume the CO, and CO2 and H2 and convert it into liquid products therein. A series of collection lines 22 withdraw fermentation liquid containing liquid products and, and depending on the type of MSBR, small amounts of cellular material from the microorganisms contained in each bioreactor 18. Where a membrane type bioreactor, of the type shown in U.S. Pat. No. 8,329,456, the contents of which are hereby incorporated reference, is used the fermentation broth passes through the MBBR on a side of the membrane opposite the microorganisms so that no cellular material is withdrawn with the fermentation broth. A line 24 transfers the fermentation liquid to the purification zones 26. Before the fermentation liquid passes to a separation zone for the recovery of liquid products, in one instance ethanol, the purification zone 26 removes, if present, any biological materials and other dissolved matter. The purification zone may use any suitable means such as filtration or ultra-filtration to recover these materials. Microorganisms retained in the purification zone may be returned to the bioreactors. After purification, the rest of the fermentation liquid passes to a liquid product separation zone via a line 27, such as for the recovery of ethanol. Fermentation liquid recovered from the liquid product separation zone returns to the bioreactors 18 via return line 28 and distribution lines 30.

In the process, described in general terms above, a collection line 32 recovers the off gas from bioreactors 18 and delivers the off gas to a vapor/liquid contacting tower, or scrubber, 40. In the scrubber, the off gas is contacted with an aqueous sulfite solution to effect the conversion of hydrogen sulfide to sulfur compounds that are beneficial to the microorganisms and the removal of any other unwanted compounds from the off gas. A line 43 provides for the addition of an aqueous sulfite solution to deliver the sulfite solution to the contacting tower 40. Optionally, a portion of the fermentation liquid recovered from the liquid product separation zone returns to the scrubber 40 via return line 42 as a separate liquid product or as a portion of the recovered liquid returned via line 28.

Non-limiting examples of sulfite addition can be as follows: directly to the scrubber 40 as an aqueous solution, to the fermentation liquid recovered from the liquid product separation zone, or indirectly through addition to the circulating scrubber water that reacts with or sequesters hydrogen sulfide. Where desired sulfite addition can be accomplished by dissolving sodium sulfite ($Na_2SO_3$) in aqueous streams to form an aqueous sulfite solution.

The hydrogen sulfide concentration in the bioreactor off gas depends on the overall bioconversion configuration, but for a typical natural gas derived syngas the concentration range is about 10 to 150 ppm. In processes of the invention, hydrogen sulfide concentration in the bioreactor off gas can be measured by a sensor 48. Such sensors are known in the industry and include light based analyzers, gas chromatograph, mass spectrometer devices, and so forth. In other embodiments of the invention, the hydrogen sulfide concentration of the washed or scrubbed off gas 44 can be measured. As known in the industry, the measured hydrogen sulfide concentration can be used to adjust sulfite addition rates, for example as represented by control valve 49. In this instance, sensed hydrogen sulfide concentration in the bioreactor off gas is used to adjust the sulfite solution addition rate to the scrubber 40. In yet other embodiments, a sulfite solution is made by dissolving $Na_2SO_3$ into an aqueous component. In these inventions, the measured hydrogen sulfide concentration in either the raw or cleaned bioreactor off gas can be used to adjust $Na_2SO_3$ addition rate.

The aqueous scrubber effluent, which includes various sulfur compounds that includes adjuvants for the anaerobic fermentation, passes through line 46. Because the aqueous scrubber effluent contains nutrients and adjuvants for anaerobic fermentation, the scrubber effluent, or a portion thereof, can be returned to the bioreactors to provide at least part of the microorganism sulfur demand and make-up water. Optionally, or when desirable, the aqueous scrubber effluent can be disposed of in an environmentally acceptable manner. Also, in some embodiments, sulfite solution addition rate to the tower can be adjusted to meet a desired level of sulfur compounds in the scrubber effluent based on using the effluent as feeds in either subsequent fermentation or biological treatment steps. In yet other embodiments, sulfite addition rate can be adjusted based on bioreactor feed stock limitations and requirements.

Treated bioreactor off gas, which exits the scrubber via line 44, can be combusted to supply a portion of plant energy requirements. While the processes of this invention attempts essentially complete removal of the hydrogen sulfide from the bioreactor off gas, any remaining gaseous sulfur compounds in the off gas, such as hydrogen sulfide, may have to be converted to $SO_x$ during combustion depending on environmental requirements. Conventional $SO_x$ removal techniques such as wet lime processes can be employed as needed. However, in some embodiments of the invention, sulfite addition can be used to adjust bioreactor off gas hydrogen sulfide content so as to meet environmental standards required to avoid the investment and operation costs of $SO_x$ removal.

Figure 2:
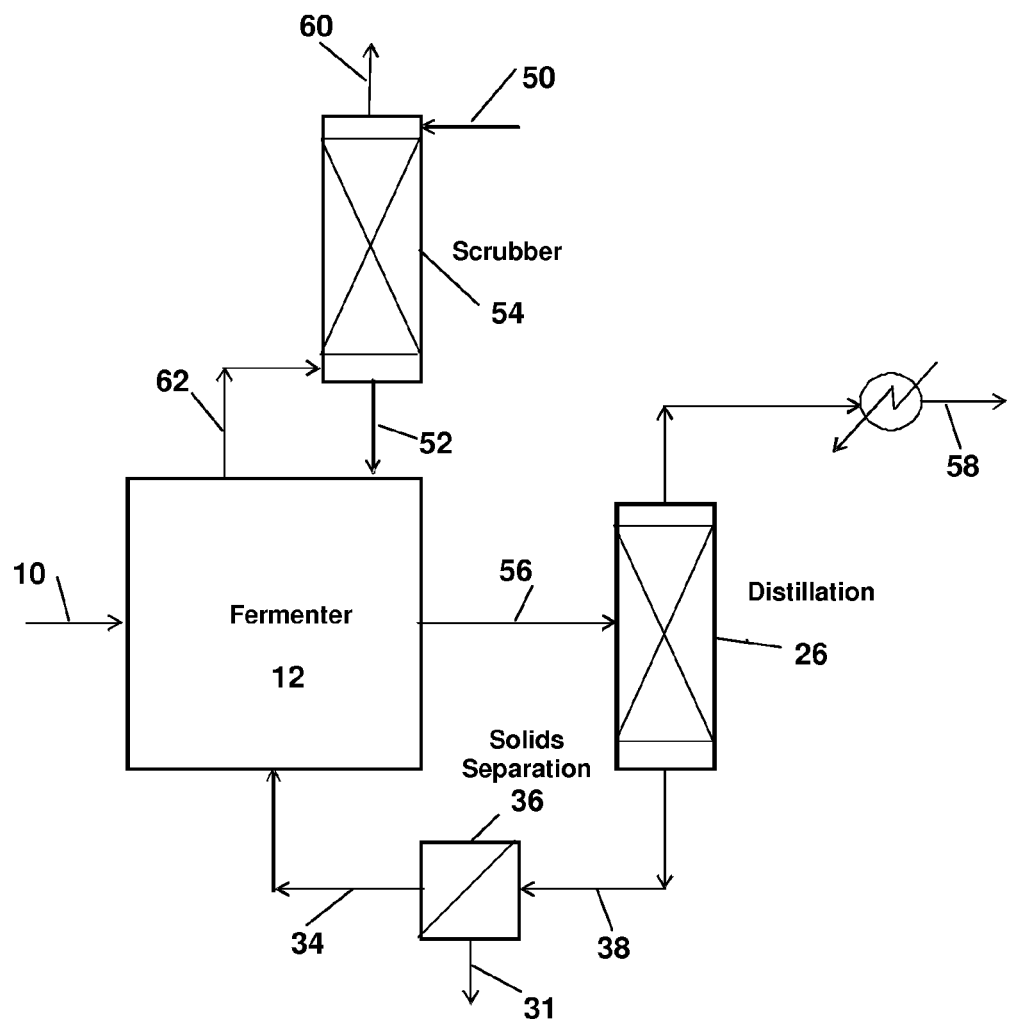
FIG. 2 is a schematic depiction of an alternate apparatus suitable for practicing the processes of this invention.

A non-limiting example of an embodiment of the invention, which is shown in FIG. 2, is summarized in the table that follows. The example is based on the commercial production of about 150,000 gallons of ethanol per year. In the example, the major gas components of the fresh, clean substrate enters the fermenter 12 via line 10 to produce liquid fuel components. In the example the hydrogen rich substrate is over 70% hydrogen on a molar basis. Besides the substrate, sulfur compounds, as described herein, useful to the bioreactor microorganisms are also fed to bioreactors to maintain microorganism metabolic activity.

In the fermenter the substrate contacts the fermentation liquid in the fermenter where the microorganisms consume the H2, CO, and CO2 which are converted into liquid products. The fermentation liquid, which contains liquid products and, depending on the fermenter type, small amounts of cellular material from the microorganisms, is withdrawn from the fermenter via line 56. The fermentation liquid is transferred to the distillation section 26 where the commercial ethanol product is withdrawn via line 58. If present, any biological materials and other dissolved matter leaves the distillation section as a liquid effluent that is sent to solids separation via line 38. The solids separator 36 may use any suitable means such as filtration or ultra-filtration to recover these materials. The elemental sulfur content of the separated biomass taken out separator 36 via line 31 is about one nmole/g (dry cell weight). Microorganisms retained in the separator may be returned to the bioreactors. After purification, the rest of the effluent fermentation liquid recovered from the liquid product separation zone returns to the fermenter 12 via return line 34.

In the process, described in general terms above, a collection line 62 recovers the off gas from fermenter 12 and delivers the off gas to a vapor/liquid contacting tower, or scrubber 54. The untreated off gas contains about 150 ppm of hydrogen sulfide. Combusting the untreated off gas collected in line 62 would generated about 88 tons per of year of SOx, a level likely to require an Environmental Protection Agency Title V air permit requiring SOx removal. The time and cost of such permitting is significant. Removing the hydrogen sulfide can significantly reduce potential SOx emissions.

Fermenter off gas hydrogen sulfide content can be significantly reduced in a scrubber 54 that contacts the off gas with an aqueous sulfite solution to effect the conversion of hydrogen sulfide to sulfur compounds that are beneficial to the microorganisms and the removal of any other unwanted compounds from the off gas. A line 50 provides for the addition of an aqueous sulfite solution to the scrubber 54. For example, sodium sulfite ($Na_2SO_3$) can be dissolved in an aqueous stream to form an aqueous sulfite solution. Optionally, a portion of the fermentation liquid recovered from the liquid product in the distillation section can be introduced into the scrubber 54.

The estimated hydrogen sulfide concentration in the treated off gas leaving the scrubber via line 60 is 15 ppm. The treated off gas hydrogen sulfide content can depend on various factors such as substrate source, overall bioconversion configuration, aqueous sulfite solution sulfite addition rate and concentration, and so forth; however, for this example, about 90 percent hydrogen sulfide is removed from the untreated fermenter off gas.

The methane content of the treated off gas from the scrubber contains about 60 percent methane and has a heating value of about 15,000 But/lb which makes the off gas a useful fuel. At the estimated hydrogen sulfide concentration of 15 ppm burning the treated off gas produces an estimated equivalent of about 9 tons of SOx per year, an amount only requiring the significantly less expensive Synthetic Minor Air Permit. Thus, the use of the invention can provide a very substantial reduction in the cost of treating the effluent from the fermenter.

The aqueous scrubber effluent, which includes various sulfur compounds that includes adjuvants for the anaerobic fermentation, passes through line 52. Because the aqueous scrubber effluent contains nutrients and adjuvants for anaerobic fermentation, the scrubber effluent when returned to the fermenter provides at least part of the microorganism sulfur demand and make-up water. Optionally, or when desirable, the aqueous scrubber effluent can be disposed of in an environmentally acceptable manner.

| | Stream Number - lb moles/hr | | | | | |
|---|---|---|---|---|---|---|
| Component | 10 | 58 | 31 | 62 | 50 | 60 |
| Hydrogen | 13,487 | | | 1,349 | | 1,349 |
| Carbon Monoxide | 3,237 | | | 65 | | 72 |
| Carbon Dioxide | 1,996 | | | 54 | | 54 |
| Nitrogen | 90 | | | 90 | | 90 |
| Methane | 90 | | | 90 | | 90 |
| Sulfur (elemental analysis) | | | 124 | | | |
| Hydrogen Sulfide | | | | 0.25 | | 0.03 |
| Sodium Sulfite | | | | | 124 | |
| Ethanol (Mgal/yr) | | 2,446 (150) | | | | |

While preferred embodiments and example configurations of the invention have been herein illustrated, shown, and described, it is to be appreciated that various changes, rearrangements and modifications may be made therein, without departing from the scope of the invention as defined by the appended claims. It is intended that the specific embodiments and configurations disclosed are illustrative of the preferred and best modes for practicing the invention, and should not be interpreted as limitations on the scope of the invention as defined by the appended claims; it is to be appreciated that various changes, rearrangements, and modifications may be made therein, without departing from the scope of the invention as defined by the appended claims.

It is claimed:

1. In a continuous process for the anaerobic bioconversion of a gas substrate comprising at least one of carbon monoxide and hydrogen with carbon dioxide in an aqueous broth containing microorganisms, the microorganisms having metabolic processes that utilize sulfur in limited amounts and being suitable for converting said substrate to alcohol comprising:
   a. continuously introducing said gas substrate at one or more gas inlets of a bioreactor assembly having at least one bioreactor for containing said broth, said bioreactor having at least one gas inlet and at least one gas outlet;
   b. maintaining contact of the microorganisms with the gas substrate and said broth to provide an alcohol-containing broth and a substrate depleted gas phase at the at least one gas outlet of said bioreactor assembly, said duration of contact being sufficient to convert at least about 80 percent of any carbon monoxide in the gas substrate to alcohol;

c. continuously or intermittently withdrawing a portion of said broth from said bioreactor assembly for recovery of said alcohol, said withdrawal being sufficient to maintain the alcohol in said broth below a concentration that unduly adversely affects the microorganisms;

d. continuously withdrawing the substrate depleted gas phase from said bioreactor assembly at said at least one gas outlet wherein the substrate depleted gas phase being withdrawn from the bioreactor assembly contains hydrogen sulfide;

e. converting at least a portion of the hydrogen sulfide from the substrate depleted gas phase to form sulfur compounds that include sulfur compounds that are beneficial to microorganisms in the bioreactor; and f. introducing at least a portion of at least the sulfur compounds that are beneficial to the microorganisms to at least one or more inlets of the bioreactor assembly.

2. The process of claim 1, wherein the bioreactor assembly is a MSBR (membrane type bioreactor) or a BCBR (bubble column bioreactor).

3. The process of claim 2, wherein the gas substrate comprises syngas from a steam reformer and contains at least about 80 mole percent carbon monoxide, hydrogen and carbon dioxide.

4. The process of claim 1, wherein the bioreactor assembly comprises at least two bioreactors in gas flow sequence.

5. The process of claim 1, further comprising combusting at least a portion of the substrate depleted gas phase from the bioreactor assembly after having at least a portion of the hydrogen sulfide removed.

6. The process of claim 1, wherein converting the hydrogen sulfide from the substrate depleted gas phase from said bioreactor assembly includes contacting the substrate depleted gas phase with an aqueous sulfite solution to produce an effluent having sulfur compounds that include sulfur compounds that are beneficial to microorganisms in the bioreactor.

7. The process of claim 1 further comprises contacting the substrate depleted gas phase from said bioreactor assembly with a recovered liquid product produced during the recovery of said alcohol from said broth.

8. The process of claim 7, wherein the recovered liquid product produced during the recovery of said alcohol from said broth comprises at least one of water, ethanol, propanol, propionic acid, acetic acid, butanol, or butyric acid.

9. The process of claim 6, wherein a system for contacting substrate depleted gas phase from said bioreactor assembly with an aqueous sulfite solution is a vapor liquid contacting device selected from the group consisting of a packed tower, a spray tower, scrubbers, and combinations thereof.

10. The process of claim 6, wherein the aqueous sulfite solution comprises at least one of sodium sulfite, sulfite, bisulfite, metabisulfite, sodium bisulfite, sodium metabisulfite, and potassium metabisulfite.

11. The process of claim 6, wherein a sulfur compound concentration of the effluent is below the concentration that unduly adversely affects the microorganisms in the bioreactors.

12. The process of claim 1, further comprising measuring at least one indicator of hydrogen sulfide concentration of the substrate depleted gas phase from said bioreactor assembly either before or after hydrogen sulfide removal.

13. The process of claim 12, wherein a device for measuring at least one indicator of hydrogen sulfide concentration is selected from a group consisting of a light analyzer, a gas chromatograph, a mass spectrometer, and combinations thereof.

14. The process of claim 13, wherein the hydrogen sulfide concentration of the substrate depleted gas phase from said bioreactor assembly before hydrogen sulfide conversion is about 10 to about 150 ppm.

15. The process of claim 12, further comprising adjusting hydrogen sulfide conversion based on the at least one indication of hydrogen sulfide concentration of the substrate depleted gas phase from said bioreactor assembly.

16. The process of claim 15, wherein adjusting hydrogen sulfide conversion based on the at least one indication of hydrogen sulfide concentration of the substrate depleted gas phase from said bioreactor assembly includes adjusting an addition rate and/or a sulfite concentration of a sulfite solution that contacts the substrate depleted gas phase from said bioreactor assembly.

17. The process of claim 1, wherein the microorganisms contained in the broth comprises a mono-culture or a co-culture of at least one of *Clostridium ragsdalei, Butyribacterium methylotrophicum, Clostridium Ljungdahlii, Clostridium autoethanogenum, Clostridium Coskatii,* and *Clostridium carboxydivorans*.

* * * * *